(12) United States Patent
Dwyer et al.

(10) Patent No.: US 7,248,985 B2
(45) Date of Patent: Jul. 24, 2007

(54) ACOUSTIC SIGNATURE TESTING FOR ELECTRONIC, ELECTROMECHANICAL, AND MECHANICAL EQUIPMENT

(75) Inventors: Michael D. Dwyer, Seminole, FL (US); Albert L. West, Tampl, FL (US); Dean R. Hellickson, Palm Harbor, FL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/095,152

(22) Filed: Mar. 31, 2005

(65) Prior Publication Data

US 2006/0229837 A1   Oct. 12, 2006

(51) Int. Cl.
   *G06F 19/00*   (2006.01)

(52) U.S. Cl. .................... 702/108; 702/48; 702/54; 702/103; 73/587; 73/594

(58) Field of Classification Search ............. 702/108, 702/103, 48, 54; 73/587, 594, 588, 589, 73/579, 583, 584, 801
See application file for complete search history.

(56) References Cited

U.S. PATENT DOCUMENTS

| | | | | |
|---|---|---|---|---|
| 4,956,999 | A | * | 9/1990 | Bohannan et al. ............. 73/587 |
| 5,191,796 | A | * | 3/1993 | Kishi et al. ................... 73/632 |
| 5,260,874 | A | * | 11/1993 | Berner et al. ................. 701/33 |
| 5,945,602 | A | * | 8/1999 | Ross ........................... 73/570 |
| 6,116,080 | A | | 9/2000 | Logue et al. |
| 6,192,739 | B1 | | 2/2001 | Logue et al. |
| 6,199,423 | B1 | | 3/2001 | Logue et al. |
| 6,279,379 | B1 | | 8/2001 | Logue et al. |
| 6,421,620 | B1 | | 7/2002 | Kotlow |
| 6,668,650 | B1 | | 12/2003 | Lafleur et al. |
| 6,964,642 | B2 | * | 11/2005 | Wasden et al. ............. 600/559 |
| 7,037,274 | B2 | * | 5/2006 | Thornton et al. ........... 600/559 |
| 2002/0183948 | A1 | | 12/2002 | Shie et al. |
| 2004/0071296 | A1 | * | 4/2004 | Wasden ....................... 381/60 |
| 2004/0073134 | A1 | * | 4/2004 | Wasden et al. ............. 600/559 |

FOREIGN PATENT DOCUMENTS

| | | |
|---|---|---|
| DE | 10132067 A1 | 1/2003 |
| EP | 20000146762 | 5/2000 |
| WO | 2004017038 A1 | 2/2004 |

OTHER PUBLICATIONS

International Search Report; Jul. 14, 2006; 5 pages.

* cited by examiner

*Primary Examiner*—Carol S. W. Tsai
(74) *Attorney, Agent, or Firm*—Evan Bundis, Esq.; Armstrong Teasdale LLP

(57) ABSTRACT

A method for testing a unit is described where the unit includes one or more of electrical, electronic, mechanical, and electromechanical components. The described method includes applying at least one stimulus to the unit, receiving sound emissions from the unit, converting the sound emissions into one or more acoustic signatures, comparing the acoustic signatures based on the received emissions to stored acoustic signatures expected as a result of the at least one stimulus, and determining a status for the unit based on the comparisons.

17 Claims, 5 Drawing Sheets

ACOUSTIC SIGNATURE TESTING FOR ELECTRONIC, ELECTROMECHANICAL, AND MECHANICAL EQUIPMENT

BACKGROUND OF THE INVENTION

This invention relates generally to testing of equipment, and more specifically to, acoustic signature fault detection for and within electronic, electromechanical, and mechanical equipment.

Currently electronic, electromechanical, and mechanical equipment, for example, equipment for aircraft and for other vehicles including navigation, tactical and other systems, are tested using measurements of voltage, current, and temperature. More specifically, such systems, sometimes referred to in the testing environment as a unit under test (UUT), are typically tested using automated test equipment. In such automated test equipment (ATE) the UUTs are subjected to a set of stimuli (applied electrical signals or mechanical inputs) that are typically experienced under operating conditions. The ATE is configured to measure one or more output conditions, electrical or mechanical, that result due to the applied stimuli. Output conditions (measurements) that are different than expected output conditions are utilized to try to determine which portion, for example, a removable circuit card, is the source of the different than expected output conditions (e.g., the failed test or fault).

However, there is still sometimes ambiguity with such testing methods. Sometimes one or more circuit cards or other subassemblies have to be removed and replaced until the source of the failed test is isolated. Some components and combinations of components emit an audible sound when operating. Others emit a sound when not operating correctly. Still others emit a frequency when one or more components or subassemblies have failed that is different than a frequency emitted when all components are operating correctly. Such audible frequency emissions are sometimes collectively referred to as acoustic signatures.

BRIEF SUMMARY OF THE INVENTION

In one aspect, a method for testing a unit, the unit including one or more of electrical, electronic, mechanical, and electromechanical components is provided. The method comprises applying at least one stimulus to the unit, receiving sound emissions from the unit, and converting the sound emissions into one or more acoustic signatures. The method further comprises comparing the acoustic signatures based on the received emissions to stored acoustic signatures expected as a result of the at least one stimulus, and determining a status for the unit based on the comparisons.

In another aspect, a unit configured to allow acoustic signature testing of the unit during operation of the unit. The unit comprises at least one microphone located within the unit and a processor configured to receive and process signals originating from the microphone. The processor is programmed to communicate with an external system regarding the processed signals.

In still another aspect, a method for configuring a unit for acoustic signature testing is provided. The method comprises embedding one or more microphones within the unit, configuring a processing device within the unit to receive inputs from the one or more microphones, and programming the processing device to communicate data regarding received inputs to an external system.

DETAILED DESCRIPTION OF THE INVENTION

Figure 1:
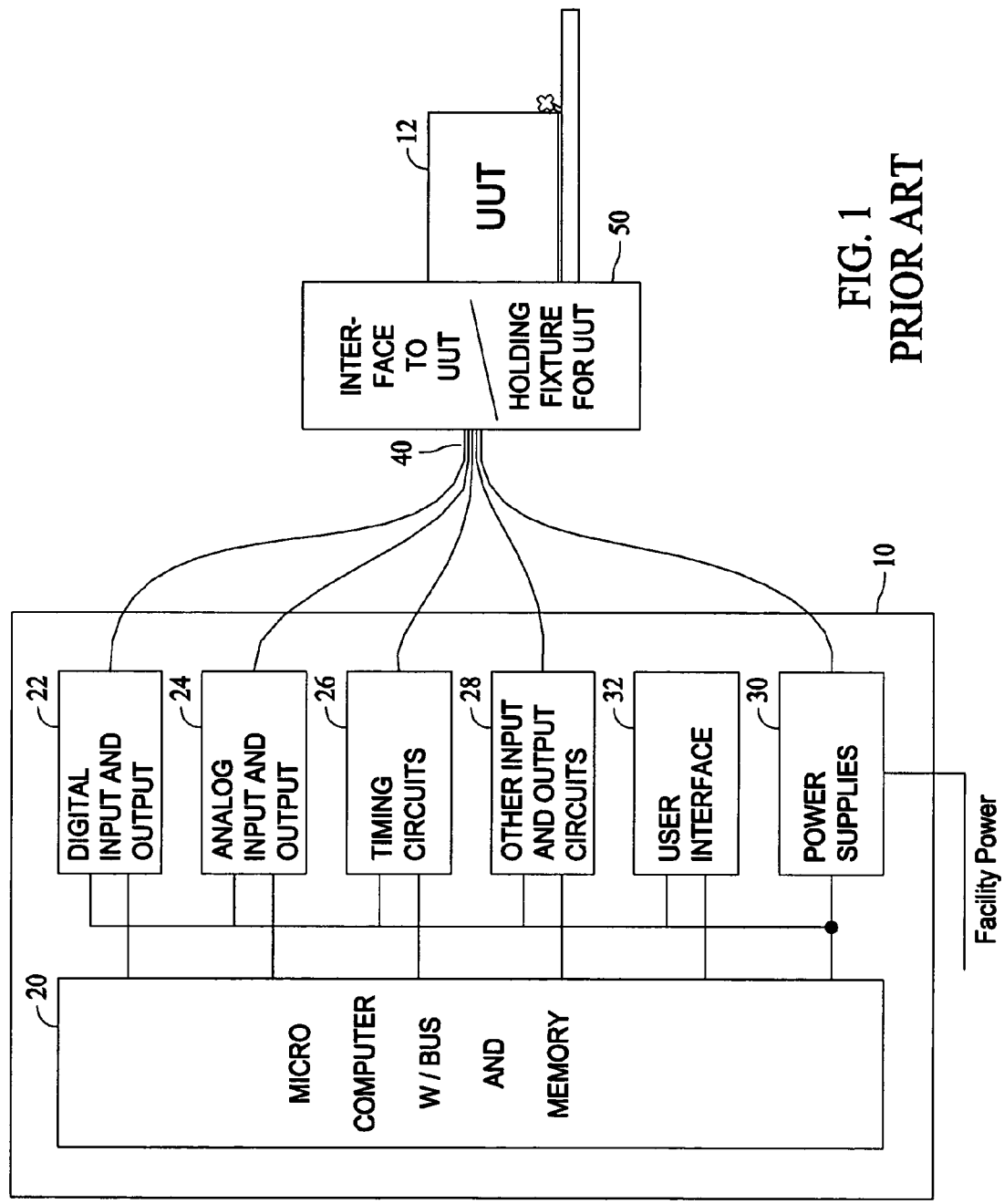
FIG. 1 is a block diagram illustrating test equipment connected to a unit under test (UUT) for testing of the UUT.

FIG. 1 is a block diagram illustrating a connection between automated test equipment (ATE) 10 and a unit under test (UUT) 12. ATE 10 typically includes a microcomputer 20 or other processing device which is bussed to control operation of and receive data from input/output circuits. Examples of input/output circuits include digital input and output 22, analog input and output 24, timing circuits 26, and other input and output circuits 28. As an example, other input and output circuits 28 may include specialized circuits providing an interface to unique circuits within a particular UUT 12. Examples of specialized circuits includes synchros and resolvers. While not shown, ATE 10 and microcomputer 20, depending upon the requirements for testing a particular UUT 12, may also incorporate and control operation of a mechanical interface which exists on a particular UUT 12. An example of such an interface may include an interface to a gear assembly extending from UUT 12.

ATE 10 further includes power supplies 30 configured to provide the various voltages and currents needed to operate microcomputer 20, the input/output circuits, and user interface 32. User interface 32 provides the interface that allows a user to operate ATE 10 for the testing of UUT 12. A wiring harness 40 is utilized to connect ATE 10 to UUT 12. Certain UUTs have additional operating requirements, for example, forced air cooling. For such UUTs, a holding fixture 50 is configured to mate with wiring harness 40. Holding fixture 50 is configured to provide the forced air cooling (not shown) to UUT 12 and further provides an enclosure that may be utilized for UUT specific interfaces (not shown), controlled by ATE 10, that are not included within ATE 10.

While ATE 10, wiring harness 40, and holding fixture 50 provide most of the parametric testing for most UUTs, certain UUTs exhibit characteristics during operation that may provide information as to whether there is an operational problem or the potential for a future operational problem therein. Specifically, certain UUTs emit sounds, which are sometimes audible, during start up sequences and/or during operation. A change to the frequency or volume of such sound may provide information as to what portion of the UUT is, or is not, operating properly. Further, certain UUTs do not emit an audible sound when properly operating. Emission of sound by such UUTs may be an indication that a portion of the UUT is not operating properly. Still further, for UUTs that emit a sound during operation, a lack of sound emissions may also provide information as to which portion of the UUT is not operating properly.

Figure 2:
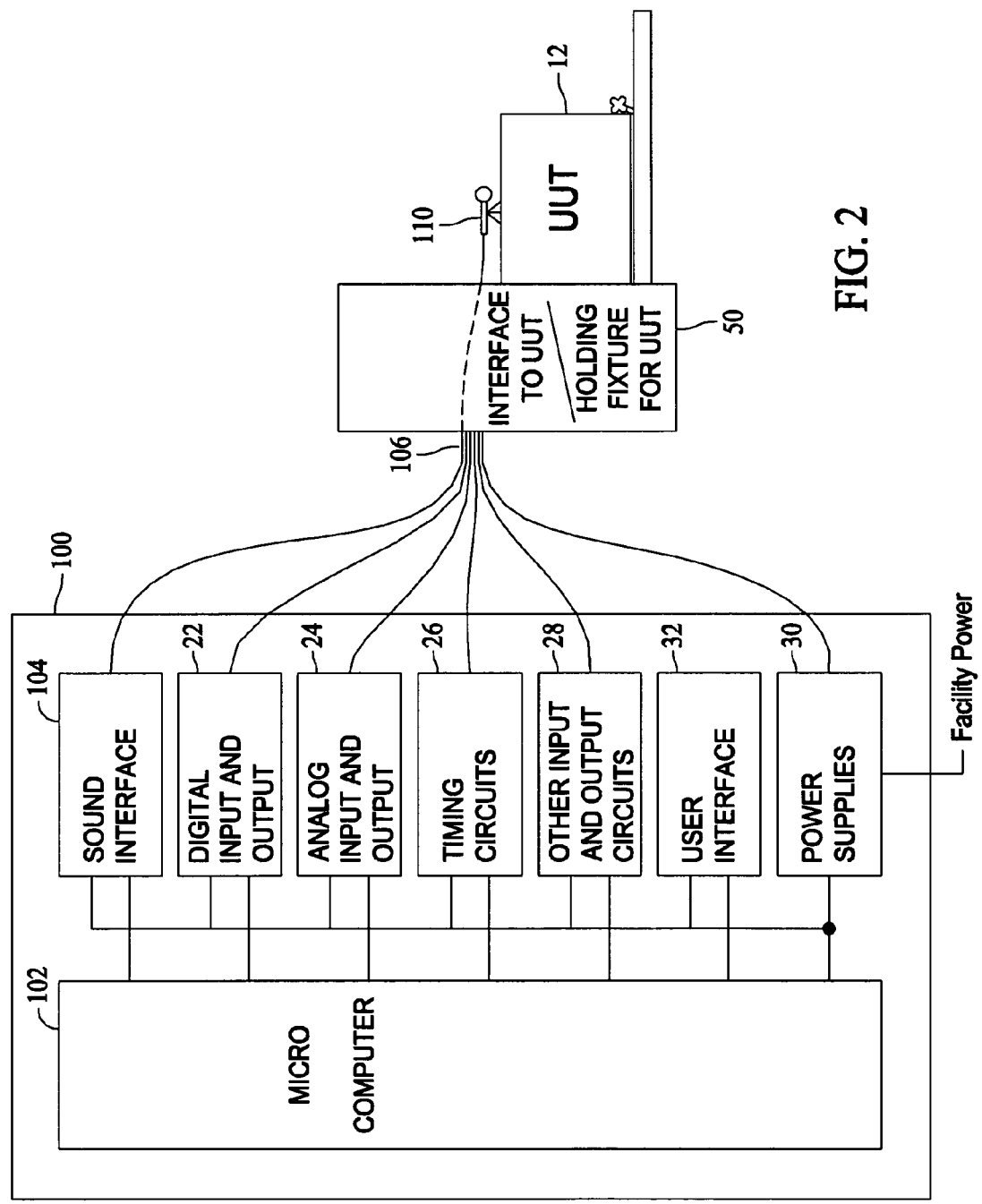
FIG. 2 is a block diagram of the test equipment of FIG. 1 incorporating acoustical testing.

FIG. 2 is a block diagram of ATE 100 that adds an acoustic signature diagnostic tool to the testing functionality provided by known ATE, for example, ATE 10. ATE 100 is configured to provide evaluation of auditory characteristics, for example, amplitude, length of time, and frequency, not currently evaluated by ATE systems testing UUTs. As such, ATE 100 may use an acoustic signature of the equipment under test, for example UUT 12, to aid in the diagnostics of the equipment or unit under test. In one embodiment, a microcomputer 102 within ATE 100 is additionally configured with one or more routines to detect anomalies in the acoustic signatures emanating from UUTs that are indicative of a failure within the UUT. Similarly, an acoustic signature can also be utilized, at least partially, to determine that the UUT is operating properly.

ATE 100 also incorporates all of the previously described functionality of ATE 10 and similar components are illustrated using the same reference numerals utilized in FIG. 1. ATE 100 further incorporates a sound interface 104 that communicates with microcomputer 102. In one embodiment, sound interface 104 communicates with microcomputer 102 utilizing the same bus structure as does the previously described input and output circuits. One example of a sound interface 104 is a digital computer sound card input. Extending from sound interface 104 is a portion of a wiring harness 106. Wiring harness 106 additionally provides an interface between the input and output circuits, including power supplies 30, of ATE 100 and holding fixture 50. As previously described, holding fixture 50 is configured for attachment of UUT 12 and to provide connection to the input and output circuits of ATE 100.

In the embodiment illustrated, extending from holding fixture 50 (and electrically connected to wiring harness 106) is a microphone 110. In an alternative embodiment, for example for retrofitting to existing ATE, a connection between sound interface 104 and microphone 110 may be separate from wiring harness 106.

In one example embodiment, UUT 12 is an inertial measurement unit (IMU). In the example embodiment, microphone 110 is a sensitive microphone placed near the IMU under test. Microphone 110 is placed in close proximity to the IMU and attached to a digital computer sound card input. ATE 100 is configured with a software program used to capture a resulting acoustic signature, for example, created during a power up sequence of the IMU. In addition, ATE 100 may be further configured to measure acoustic outputs of UUT 12 during specific portions of the test program as the operating capabilities of UUT 12 are tested.

Figure 3:
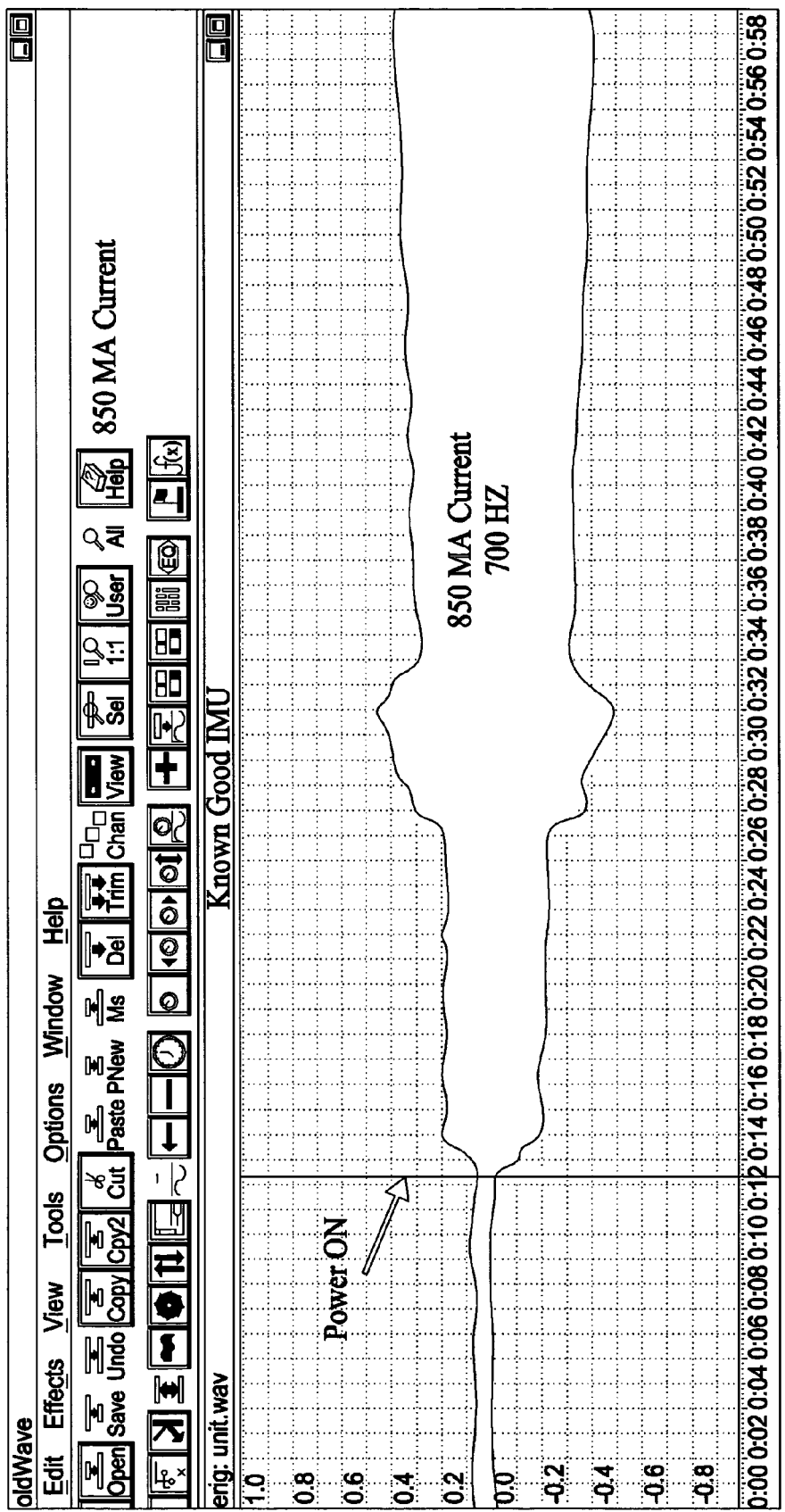
FIG. 3 is a graph illustrating certain acoustic signatures for a known good inertial measurement unit.
Figure 4:
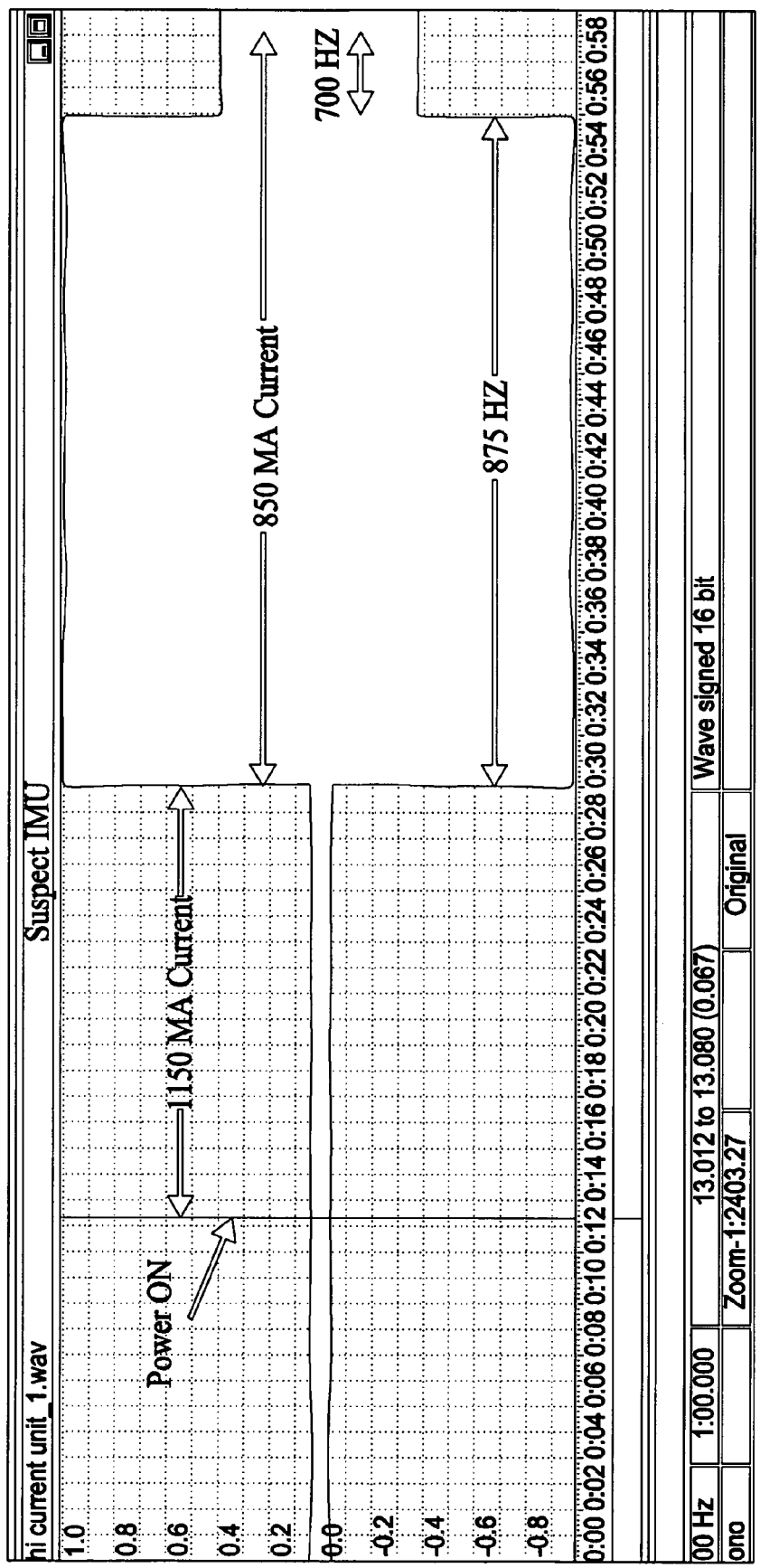
FIG. 4 is a graph illustrating the same acoustic signatures as illustrated in FIG. 3 for a suspect inertial measurement unit.

To illustrate capabilities of ATE 100, FIG. 3 is a graph 150 illustrating a portion of an audible output for a known good IMU. Graph 150 illustrates an amplitude of sound over time emitted by the IMU during the power up sequence and the beginning of communications with external systems. However, FIG. 4 is a graph 200 illustrating the same audible outputs as illustrated in FIG. 3 for a suspect IMU. In this particular IMU, a five volt power supply is not operational. After about 30 seconds, a dither motor within the IMU becomes saturated and begins to oscillate. The audible sound created by this oscillation is shown in graph 200 as a 875 Hz signal. By receiving the 875 Hz signal through microphone 110, ATE 100 is capable of determining that the five volt power supply has failed without having to make a series of signal measurement as is done utilizing current testing methods.

Figure 5:
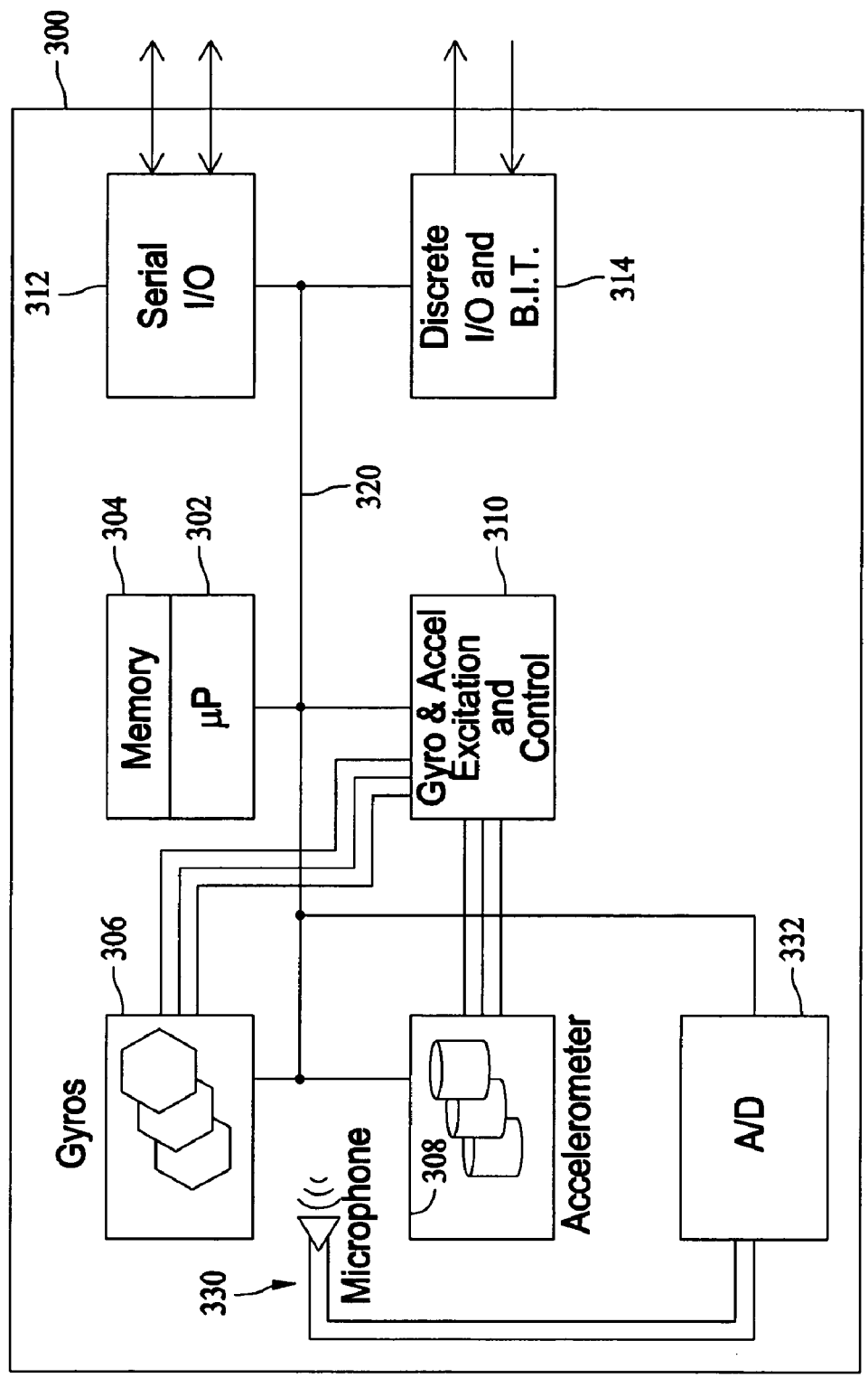
FIG. 5 is a block diagram of an inertial measurement unit configured for acoustic signature testing.

While described in terms of an ATE application, the acoustic signature testing methods described herein may also be implemented within the various products, for example IMUs, themselves. FIG. 5 is a block diagram of an IMU 300 which incorporates the above described acoustic signature sampling capabilities. IMU 300 includes a microprocessor 302, memory 304, gyroscopes 306, accelerometers 308, gyro and accelerometer excitation and control circuits 310, serial input/output (I/O) circuits 312, and discrete input/output (I/O) circuits 314. In one embodiment, discrete I/O circuits 314 includes circuitry dedicated to a built in test (BIT) for IMU 300.

Gyroscopes 306, accelerometers 308, gyro and accelerometer excitation and control circuits 310, serial I/O circuits 312, and discrete I/O circuits 314 communicate with microprocessor 302 over a bus 320. IMU 300 further includes power supply circuits 322 which provide the various power sources utilized by the other components of IMU 300. In the embodiment illustrated, IMU 300 further includes a microphone sensor 330 located in proximity to gyroscopes 306 and accelerometers 308. Microphone sensor 330 is configured to provide signals to an analog-to-digital (A/D) converter 332 which digitizes the analog signals received from microphone sensor 330 and outputs those signals to bus 320 for receipt by microprocessor 302. After analysis of such signals, microprocessor 302 is configured to provide a result of such analysis to external systems, for example, by communicating the analysis through serial I/O 312. As used herein, the term microprocessor is understood to include all devices capable of processing programmed instructions. In a specific embodiment, microprocessor 302 is a microcontroller which incorporates the functions of A/D converter 332 internally.

Incorporation of microphone 330 and A/D converter 332 provide another testing function that can be incorporated into a prognostic health management system stored in memory 304 and running on microprocessor 302. Such an embodiment might include, for example, measurements of sound levels and frequencies for a known good IMU that are stored within IMU 300. Comparison of the acoustic signature for the known good IMU are then compared to measurement taken within IMU 300, for example, during power up sequences and may include periodic measurements of sound levels during operation. If the sound levels and frequencies vary from expected levels and frequencies stored within IMU 300, microprocessor 302 is programmed to communicate those measurements to an external system for either storage or further analysis (by either a user or the external system). Upon completion of the analysis, it is communicated to the proper persons, for example, those who provide maintenance for the systems which employ IMUs 300. The communication may also include the possible causes for the uncharacteristic levels and/or frequencies generated within the IMU 300.

While microphone 330 is described herein as being in proximity to gyroscopes 306 and accelerometers 308, it is to be understood that such an embodiment is only one example. Microphones providing signals to A/D converters might be utilized in several places within an IMU to provide information regarding failed, or likely to fail components. As such, operators, for example those familiar with IMU designs, can use the acoustic signature, perhaps in graphical form, (i.e., amplitude, time, frequency) to determine the failure mode within the IMU and act accordingly.

While described herein in terms of a microphone receiving audio signals, other embodiments utilize devices other than microphones to determine the presence of an acoustic signature or other vibrational characteristics. Specifically, and in one embodiment, a low level laser beam is reflected from a surface, for example, a gimbal in an inertial measurement unit. The reflection is demodulated, which exposes any changes in vibration.

While described in terms of an example IMU, the above descriptions should not be construed as being so limited. Many other products and subassemblies are configurable to allow the incorporation of microphones, vibration measurement devices, and A/D converters for implementation of the above described acoustic testing methods, including, but not limited to, sensor products such as ring laser gyroscopes and accelerometers, printing wiring boards, power supplies, electronic products, and mechanized products.

While the invention has been described in terms of various specific embodiments, those skilled in the art will recognize that the invention can be practiced with modification within the spirit and scope of the claims.

What is claimed is:

1. A method for testing a navigational unit, the navigational unit including one or more of electrical, electronic, mechanical, and electromechanical components, said method comprising:

applying at least one stimulus to the navigational unit;

receiving sound emissions from the navigational unit, the sound emissions resulting from the application of the at least one stimulus;

converting the sound emissions into one or more acoustic signatures;

comparing the acoustic signatures based on the received emissions to stored acoustic signatures, the stored acoustic signatures representative of acoustic signatures expected from the navigational unit due to application of the at least one stimulus; and determining a status for the navigational unit based on the comparisons.

2. A method according to claim 1 wherein receiving sound emissions from the navigational unit comprises:

placing at least one operable microphone in proximity to the navigational unit; and measuring signals received from the at least one microphone.

3. A method according to claim 1 wherein receiving sound emissions from the navigational unit comprises measuring signals received from at least one microphone embedded within the navigational unit.

4. A method according to claim 1 wherein determining a status for the navigational unit based on the comparisons comprises at least one of identifying one or more failed components within the navigational unit and identifying components within the navigational unit that appear susceptible to future failure.

5. A method according to claim 1 wherein converting the sound emissions into one or more acoustic signatures comprises:

sampling signals from a microphone using an analog-to-digital converter; and storing the samples as an acoustic signature file.

6. A method according to claim 5 wherein comparing the acoustic signatures to acoustic signatures expected comprises using a processor to compare the acoustic signature file corresponding to the signals received from the microphone to an acoustic signature file of a known good navigational unit subjected to equivalent stimuli.

7. A method according to claim 1 wherein receiving sound emissions from the navigational unit comprises:

transmitting a signal towards a portion of the navigational unit;

receiving reflections of the signal; and demodulating the reflections to determine a vibration of the portion of the navigational unit.

8. An electromechanical unit configured to allow acoustic signature testing of said unit during operation of said unit, at least one stimulus being applied to said unit during operation of said unit, said unit comprising:

at least one microphone located within said unit;

a processor configured to receive and process signals originating from said at least one microphone, said processor programmed to communicate with an external system regarding the processed signals; and a memory configured to store at least one acoustic signature representative of an acoustic signature emanated by a good unit, said processor configured to compare an acoustic signature resulting from the stimulus applied to said unit against at least one acoustic signature resulting from the same stimuli and stored in said memory.

9. A unit according to claim 8 wherein to operate said unit, at least one stimulus is applied to said unit, said processor configured to process received signals from said at least one microphone based on the one or more stimuli applied to said unit.

10. A unit according to claim 8 wherein said processor is configured to process the received signals and provide an acoustic signature, based on the received signals, to an external system.

11. A unit according to claim 8 wherein said processor is configured to determine and communicate a failure mode of said unit based on the comparison.

12. A method for configuring a navigational unit for acoustic signature testing, said method comprising:

embedding one or more microphones within the navigational unit;

configuring a processing device within the navigational unit to receive inputs from the one or more microphones;

programming the processing device to compare the received inputs with acoustic signature data stored within the navigational unit; and further programming the processing device to communicate data regarding the comparison of the stored acoustic signature data to the received inputs to an external system.

13. A method according to claim 12 wherein configuring a processing device within the navigational unit comprises:

digitizing the received inputs; and configuring the processing device to receive the digitized inputs.

14. A method according to claim 12 wherein programming the processing device to communicate data comprises:

configuring the processing device to analyze the received inputs; and communicating the results of the analysis to an external system.

15. A method according to claim 14 wherein communicating the results of the analysis comprises communicating a failure mode of the navigational unit.

16. A method according to claim 14 wherein configuring the processing device to analyze the received inputs comprises configuring the navigational unit to:

calculate an acoustic signature for the navigational unit from the received inputs; and compare the calculated acoustic signature with an acoustic signature of a good navigational unit that has been stored within the navigational unit.

17. A method according to claim 12 wherein configuring a processing device within the navigational unit to receive inputs comprises configuring the processing device to analyze sound measurements within the navigational unit taken during power up sequences of the navigational unit and periodically during subsequent operation of the navigational unit.

* * * * *